US008346375B2

(12) United States Patent
Jonsen et al.

(10) Patent No.: US 8,346,375 B2
(45) Date of Patent: Jan. 1, 2013

(54) PINCH CASE FOR DEFIBRILLATOR ELECTRODE PADS AND RELEASE LINER

(75) Inventors: Eric Jonsen, Seattle, WA (US); Patrick Hauge, Bellevue, WA (US); Zebrick Roach, Seattle, WA (US); Kurt Fischer, Lynnwood, WA (US)

(73) Assignee: Koninklijke Philips Electronics NV, Eindhoven (NL)

( * ) Notice: Subject to any disclaimer, the term of this patent is extended or adjusted under 35 U.S.C. 154(b) by 135 days.

(21) Appl. No.: 12/827,142

(22) Filed: Jun. 30, 2010

(65) Prior Publication Data

US 2011/0257695 A1  Oct. 20, 2011

Related U.S. Application Data

(63) Continuation-in-part of application No. 12/513,688, filed on Apr. 16, 2010, now Pat. No. 8,170,639.

(60) Provisional application No. 60/865,486, filed on Nov. 13, 2006.

(30) Foreign Application Priority Data

Nov. 6, 2007 (WO) .................. PCT/IB2007/054499

(51) Int. Cl.
*A61N 1/04* (2006.01)
*A61N 1/39* (2006.01)

(52) U.S. Cl. ............. 607/142; 600/372; 600/384; 607/5
(58) Field of Classification Search ............. 607/5, 142, 607/4; 600/372, 382, 384, 386, 391, 393
See application file for complete search history.

(56) References Cited

U.S. PATENT DOCUMENTS

| | | | |
|---|---|---|---|
| 6,115,638 A * | 9/2000 | Groenke | 607/142 |
| 6,694,193 B2 * | 2/2004 | Lyster et al. | 607/142 |
| 7,039,460 B2 * | 5/2006 | Ryczek | 607/5 |
| 7,489,972 B2 * | 2/2009 | Denney et al. | 607/142 |
| 7,822,488 B2 * | 10/2010 | Jonsen et al. | 607/142 |
| 2002/0117408 A1 * | 8/2002 | Solosko et al. | 206/210 |
| 2003/0055478 A1 * | 3/2003 | Lyster et al. | 607/142 |
| 2003/0065363 A1 * | 4/2003 | Faller et al. | 607/5 |
| 2005/0283219 A1 * | 12/2005 | O'Connor et al. | 607/152 |
| 2008/0097546 A1 * | 4/2008 | Powers et al. | 607/36 |
| 2008/0210592 A1 * | 9/2008 | Anderson et al. | 206/701 |
| 2009/0054939 A1 * | 2/2009 | Hansen et al. | 607/5 |
| 2009/0138059 A1 * | 5/2009 | Ouwerkerk | 607/5 |
| 2011/0230925 A1 * | 9/2011 | Copp-Howland et al. | 607/8 |

\* cited by examiner

*Primary Examiner* — Niketa Patel
*Assistant Examiner* — Christopher A Flory
(74) *Attorney, Agent, or Firm* — W. Brinton Yorks, Jr.

(57) ABSTRACT

A defibrillator electrode assembly with a slot-like storage case is described which protects the pads prior to use and retains them in either an electrically connected or electrically disconnected configuration. When the electrode assembly is slidably inserted into the case, an optional pinch clip within the case presses electrodes on opposite sides of a thick release liner into electrical contact with each other.

10 Claims, 13 Drawing Sheets

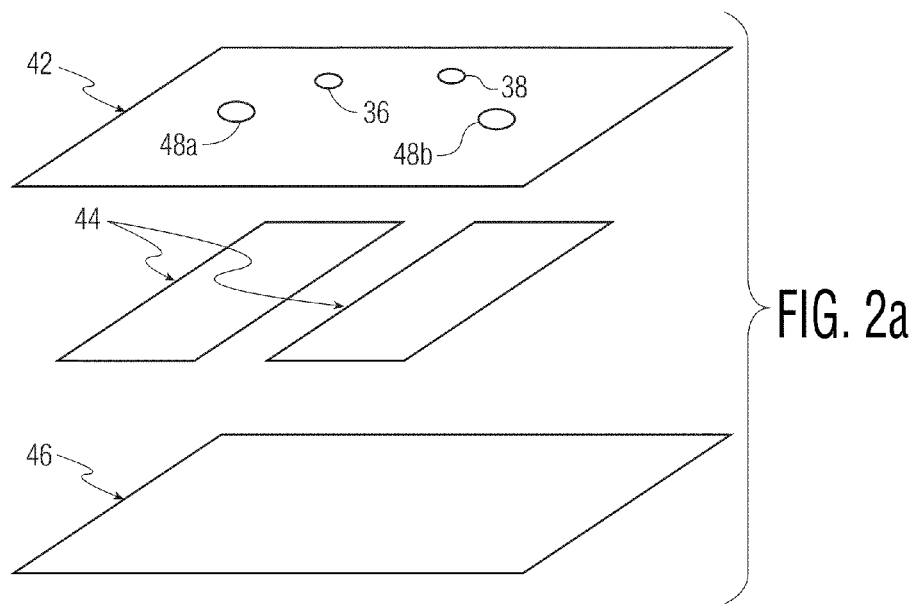
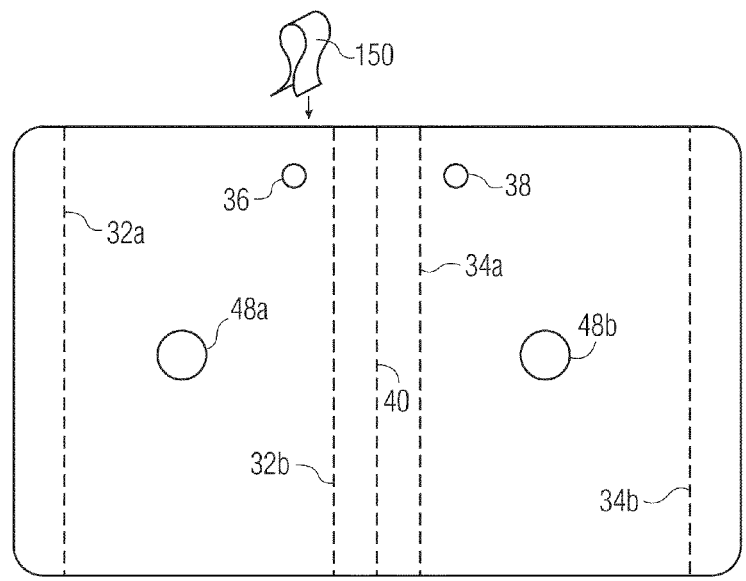
FIG. 2b

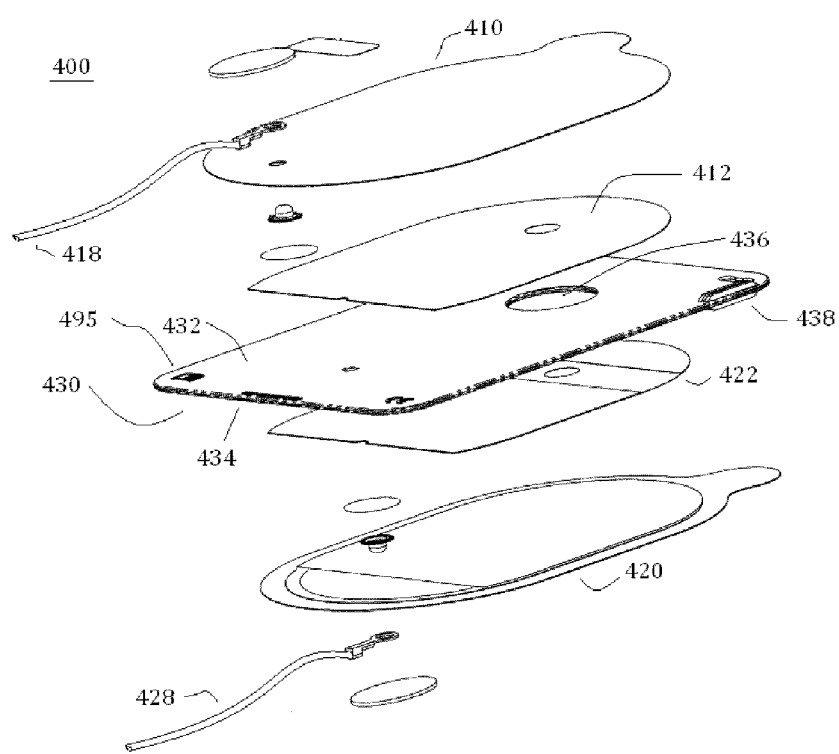

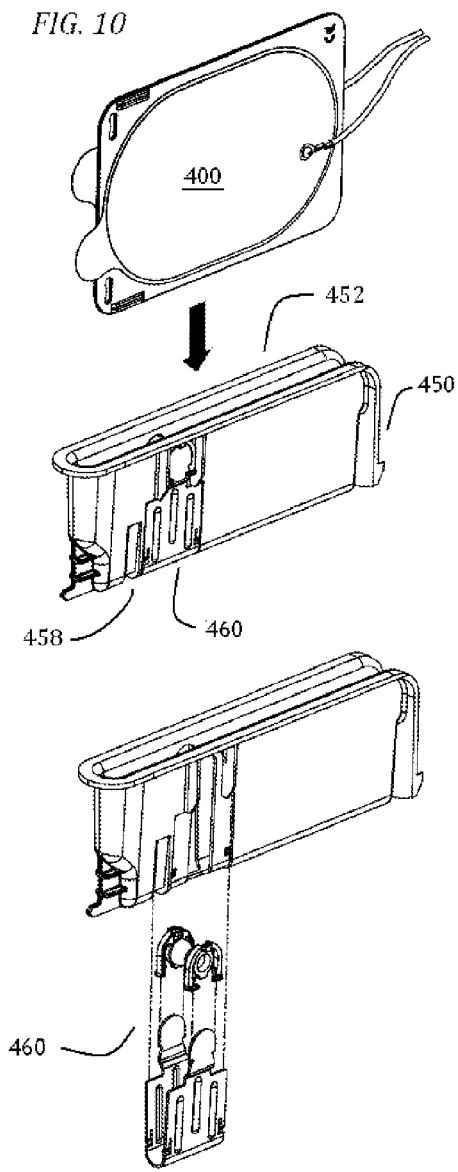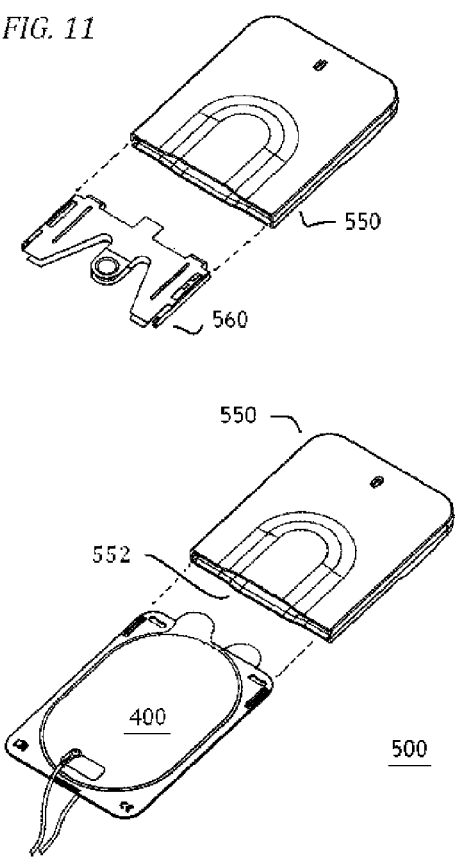

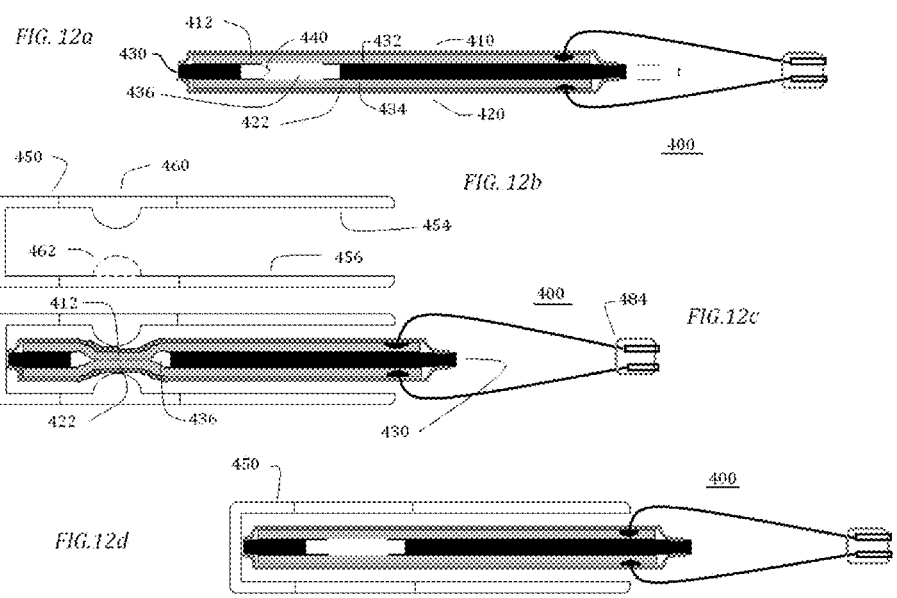

PINCH CASE FOR DEFIBRILLATOR ELECTRODE PADS AND RELEASE LINER

This application is a continuation-in-part of co-pending U.S. patent application Ser. No. 12/513,688 which is the National Stage Entry of PCT Application No. PCT/IB07/54499 filed on Nov. 6, 2007 for "CASE FOR DEFIBRILLATOR ELECTRODE PADS AND RELEASE LINER", which in turn claims the benefit of U.S. Provisional Patent Application Ser. No. 60/865,486 filed on Nov. 13, 2006.

This invention relates to defibrillators for cardiac resuscitation and, in particular, to electrode pads for defibrillators.

Cardiac arrest is a life-threatening medical condition in which the patient's heart fails to provide blood flow to support life. A defibrillator can be used to deliver defibrillating shocks to a patient suffering from cardiac arrest. The defibrillator resolves this condition by delivering a high-voltage impulse to the heart in order to restore normal rhythm and contractile function in patients who are experiencing arrhythmia such as VF (ventricular fibrillation) or VT (ventricular tachycardia) that is not accompanied by spontaneous circulation. There are several classes of defibrillators, including manual defibrillators, implantable defibrillators, and automatic external defibrillators (AEDs). AEDs differ from manual defibrillators in that AEDs can automatically analyze the electrocardiogram (ECG) rhythm to determine if defibrillation is necessary. The defibrillator analyzes the ECG signal for signs of arrhythmia. If VF is detected, the defibrillator signals the rescuer that a shock is advised. After the detection of VF or other shockable rhythm, the rescuer presses a shock button on the defibrillator to deliver a defibrillation pulse to resuscitate the patient.

External defibrillators act through electrode pads applied across the chest of the patient. The electrodes adhesively attach to the patient and are used both to acquire an ECG signal from the patient's heart and to apply the defibrillating shock. AED electrodes commonly are formed by locating a foil or metallized electrode between a flexible nonconductive backing and a conductive adhesive gel. The conductive adhesive attaches the electrode securely to the patient. Gels, however, will dry out (desiccate) over time and have a finite shelf life. A typical shelf life for an electrode with gel adhesive is about two years, after which the electrodes must be replaced. Some AEDs use electrodes which are simply replaced when the safe shelf life period has expired. Other AEDs have an internal self-test circuit which periodically tests the electrodes and detects desiccation by an impedance change. For self-test electrodes the electrodes are electrically connected to each other to form a continuous closed loop circuit that is tested. The closed loop circuit is broken when the electrode pads are deployed for use.

In the case of both self-tested electrodes and non-self-tested electrodes, it is typical that the electrodes will be connected to the AED while stored prior to use so that the rescuer does not need to connect them; they are already pre-connected and ready for use. The self-test electrodes are pre-connected with the loop circuit closed for self-testing. The non-self-test electrodes are generally not connected in a closed loop circuit while stored prior to use. Hence, two different styles of electrodes are needed for self-testing and non-self-testing defibrillators.

Our concurrently filed U.S. patent application Ser. No. 12/513,685 describes a release liner for a pair of electrodes with a moisture-impermeable surface on which the electrodes are peripherally attached, sealing the conductive gel of the electrodes between the moisture-impermeable backing of the electrodes and the moisture-impermeable surface of the release liner. The release liner also has an electrical contact electrically connected to each electrode. When the release liner is folded in a first configuration the electrical contacts are brought into contact with each other, completing an electrical connection between the two electrodes. When the release liner is not in this configuration there is no electrical connection between the two electrodes. It would be desirable to have a device which both retains the release liner and electrodes in the desired configuration and protects the release liner and electrodes prior to use.

In accordance with the principles of the present invention, a release liner for defibrillator electrode pads is described which can be used for electrode pads connected in a closed loop for self-test and for electrode pads connected in an open circuit. The release liner includes two areas where electrode pads are attached prior to use. When the electrodes are attached to the release liner the adhesive gel of each electrode is electrically connected to a conductor that provides the closed circuit for self-test electrodes. When the release liner is folded one way a closed circuit is completed between the electrodes. When not folded this way there is no closed circuit between the electrodes. In one embodiment described below a clip is provided to retain the folded release liner in either the closed circuit or open circuit configuration. In another embodiment a case is provided with an internal clip that retains the release liner and electrodes in the desired configuration. The case also protects the electrodes prior to use.

In the drawings:

FIG. 2a illustrates a first example of a release liner of the present invention in an exploded view.

FIG. 2b is a plan view of the release liner of FIG. 2a after assembly.

FIG. 5a is a perspective view of a case for a release liner and electrode of the present invention and FIG. 5b is a cross-sectional view of the case of FIG. 5a.

FIG. 9 illustrates an exploded view of another release liner and electrode embodiment constructed in accordance with the principles of the present invention.

FIG. 10 is a perspective view of a storage case embodiment for the release liner and electrode of the present invention.

FIG. 11 is a perspective view of yet another storage case embodiment for the release liner and electrode of the present invention.

FIG. 12 is a cross-sectional view of the case of either FIG. 10 or 11 with the release liner and electrode installed.

Figure 1:
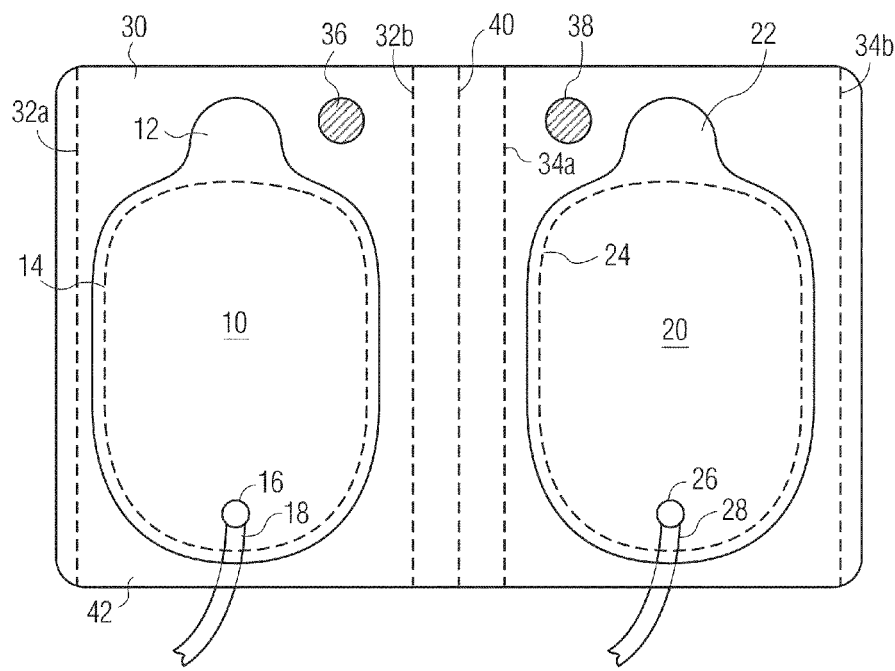
FIG. 1 illustrates a halibut-style release liner and electrodes constructed in accordance with the principles of the present invention.

Referring first to FIG. 1, a halibut-style release liner 30 and electrode set 10,20 is shown in plan view. The style is referred to as halibut-style herein by reason of the resemblance of the relatively flat, flexible electrodes 10,20 to the fish of the same name when attached to the release liner. In this view the nonconductive backing surface of the electrodes 10,20 is facing the viewer. The adhesive gel on the other side is in contact with the release surface 42 of the release liner 30. A wire 18,28 is connected through the backing of each electrode 10,20 to the inner conductive layer of the electrode and is held in place by a fastener such as a rivet 16,26. Desiccation of the gel is retarded by sealing the nonconductive backing of each electrode to the moisture impermeable release surface 42 of the release liner. The seals 14, 24 are made around the periphery of the gel areas of the electrodes. A tab 12, 22 is formed at the end of the backing of the electrodes and may be grasped by a user to pull the electrodes away from the release liner when they are to be used.

Located inside the release liner 30 under each electrode 10,20 is a conductive sheet 44 (see FIG. 2) of metallic foil or other thin conductive material. The lateral extent of each sheet is indicated by dashed lines 32a,32b and 34a,34b. A hole 36, 38 is formed in the outer release surface layer 42 to give access to each conductive sheet. It is seen that each side of the halibut release liner of FIG. 1 is a mirror image of the other about the center fold line 40 of the release liner 30. In accordance with the principles of the present invention, when the two sides are folded up and toward each other, the hole 36 will be opposite the hole 38 so that the conductive sheets visible through the holes can be brought into electrical contact with each other. When the release liner remains flat as shown in the drawing or when folded back along the fold line 40 so that the back sides (not visible in FIG. 1) are brought into contact with each other, there is no contact or electrical connection of the sheets within the release liner.

FIGS. 2a and 2b illustrate how the manner in which the release liner is folded dictates whether an open circuit or closed circuit is formed with the electrodes. In the exploded view of FIG. 2a, the nonconductive release surface layer 42 is seen to have four holes in it, the two previously described access holes 36,38 for the inner conductive sheets 44 and two holes 48a and 48b which underlie the electrodes when they are sealed to the layer 42.

The bottom layer of the release liner is a nonconductive layer 46. Between the layers 42 and 46 are the two conductive sheets 44 which underlie the electrode positions and holes 36,38 on each side of the release liner. When the conductive sheets are sealed between layers 42 and 46 their lateral sides in this example are positioned as shown by dashed lines 32a,32b for the left side conductive sheet and dashed lines 34a,34b for the right side conductive sheet as shown in FIG. 2b. Referring to FIG. 1 and FIG. 2b, it is apparent how the electrodes 10,20 can be electrically connected together. When the release liner is folded along fold line 40 so that the left and right upper sides are brought into contact with each other, an electrical circuit is completed between the wire 18 of the left electrode 10, the conductive layer of that electrode, its gel layer which is in contact with the left conductive sheet 44 of the release liner through the hole 48a, through holes 36 and 38 and the contact between the left and right conductive sheets 44 through those holes, from the right conductive sheet to the gel of the right electrode 20 through hole 48b, to the conductive layer of the electrode 20 and to its wire 28. When the two wires 18,28 are connected to a defibrillator a closed loop circuit is thus formed with the defibrillator. To keep the left and right conductive sheets 44 in electrical contact with each other when the release liner is folded closed in this configuration, a clip 150 or other fastening device may be applied to pinch the two conductive sheets 44 into contact with each other through holes 36 and 38 as shown in FIG. 2b. Other alternative holding techniques may be used such as fastening the sheets with a conductive adhesive when holes 36 and 38 are brought into contact with each other. In this closed loop circuit configuration the electrodes may be readily self-tested by signals applied by the defibrillator to which wires 18 and 28 are connected.

When the release liner and electrode are to be connected to a defibrillator which does not require closed loop connection of the electrodes it is sufficient that the conductive sheets visible through the holes 36 and 38 not be brought into contact with each other. The release liner can be folded the opposite way with the back sides of the release liner (layer 46) in contact with each other. If desired the clip 150 can be used to retain the release liner in this folded configuration. The release liner can alternatively be left unfolded as it is in FIGS. 1 and 2b.

Variations of this example will be readily apparent to those skilled in the art. For instance the conductive sheets 44 do not need to have the shape illustrated in this example; they can simply be conductors between the electrode hole 48a and the access hole 36 and between electrode hole 48b and access hole 38. One of the electrodes could be located on the other side (the layer 46 side) of the release liner provided that the electrode hole for that electrode were on that side of the release liner. The holes 36,38 could be punched through the release layer 42 but the punched material not removed unless the closed loop configuration were to be employed. Separate insulating covers could be used over one or both of the holes 36,38 to prevent electrical connection between the two conductive sheets 44 even in the forward folded condition. Other variations are also possible.

Figure 3:
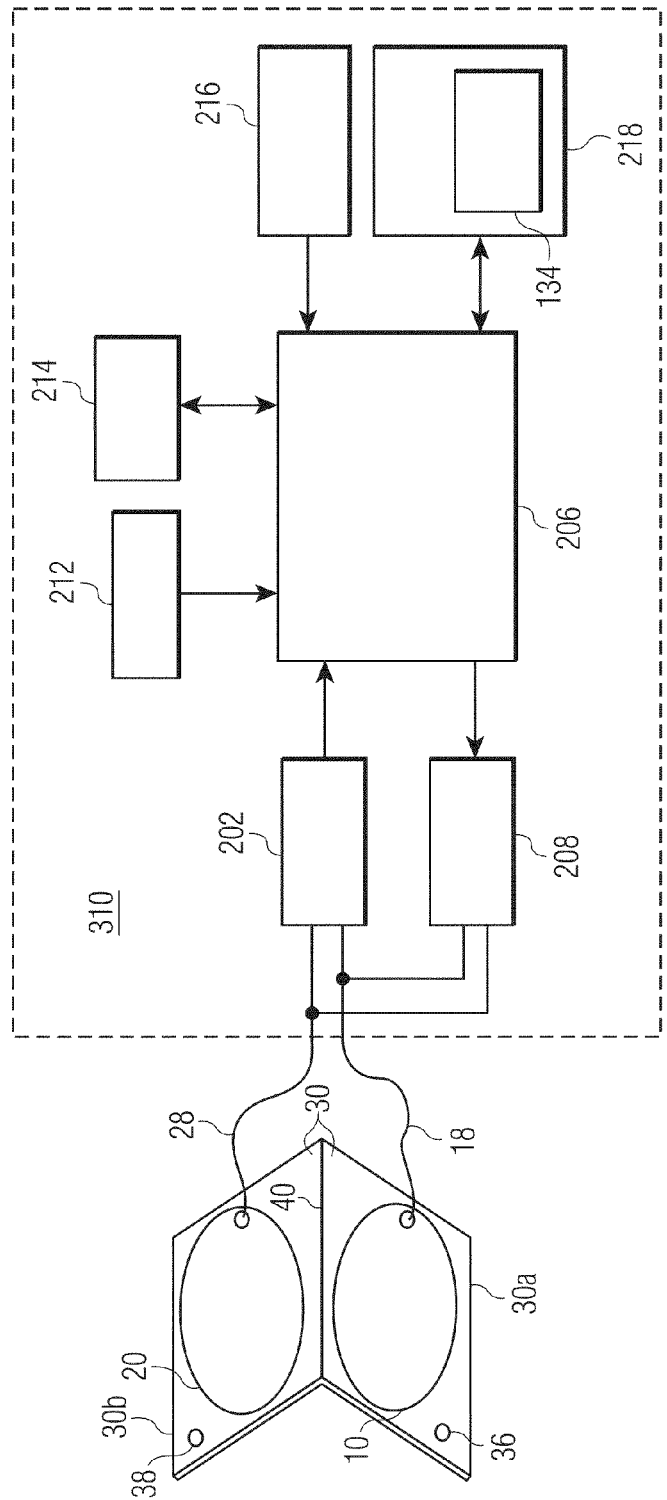
FIG. 3 illustrates a halibut-style release liner and electrodes connected to a defibrillator.

FIG. 3 shows the halibut release liner and electrodes when connected to a defibrillator 310. An ECG front end circuit 202 is connected to the wires 18,28 of the electrodes 10,20. In FIG. 3 the electrodes 10,20 are shown peripherally attached to the two sides 30a,30b of the release liner 30 prior to being peeled off of the release liner and attached to the patient. The ECG front end circuit 202 operates to amplify, buffer, filter and digitize an electrical ECG signal generated by the patient's heart and picked up by the electrodes to produce a stream of digitized ECG samples. The digitized ECG samples are provided to a controller 206 that performs an analysis to detect VF, shockable VT or other shockable rhythm. If a shockable rhythm is detected, the controller 206 sends a signal to HV (high voltage) delivery circuit 208 to charge a high voltage capacitor of circuit 208 in preparation for delivering a shock, and a shock button on a user interface 214 is activated to begin flashing. The rescuer 220 is then advised by an audible instruction to keep away from the patient ("hands off" instruction). When the rescuer presses the shock button on the user interface 214 a defibrillation shock is delivered from the HV delivery circuit 208 to the patient through the electrodes 10,20.

The controller 206 is coupled to further receive input from a microphone 212 to produce a voice strip. The analog audio signal from the microphone 212 is preferably digitized to produce a stream of digitized audio samples which may be stored as part of an event summary 134 in a memory 218. The user interface 214 may consist of a display, an audio speaker, and control buttons such as an on-off button and a shock button for providing user control as well as visual and audible prompts. A user interface of the present invention may also include one or more control buttons for selecting a rescue protocol stored in memory 218 to be carried out during a rescue. A clock 216 provides real-time or elapsed time clock data to the controller 206 for time-stamping information contained in the event summary 134. The memory 218, implemented either as on-board RAM, a removable memory card, or a combination of different memory technologies, operates to store the event summary 134 digitally as it is compiled during the treatment of the patient 210. The event summary 134 may include the streams of digitized ECG, audio samples, and other event data as previously described.

Figure 4:
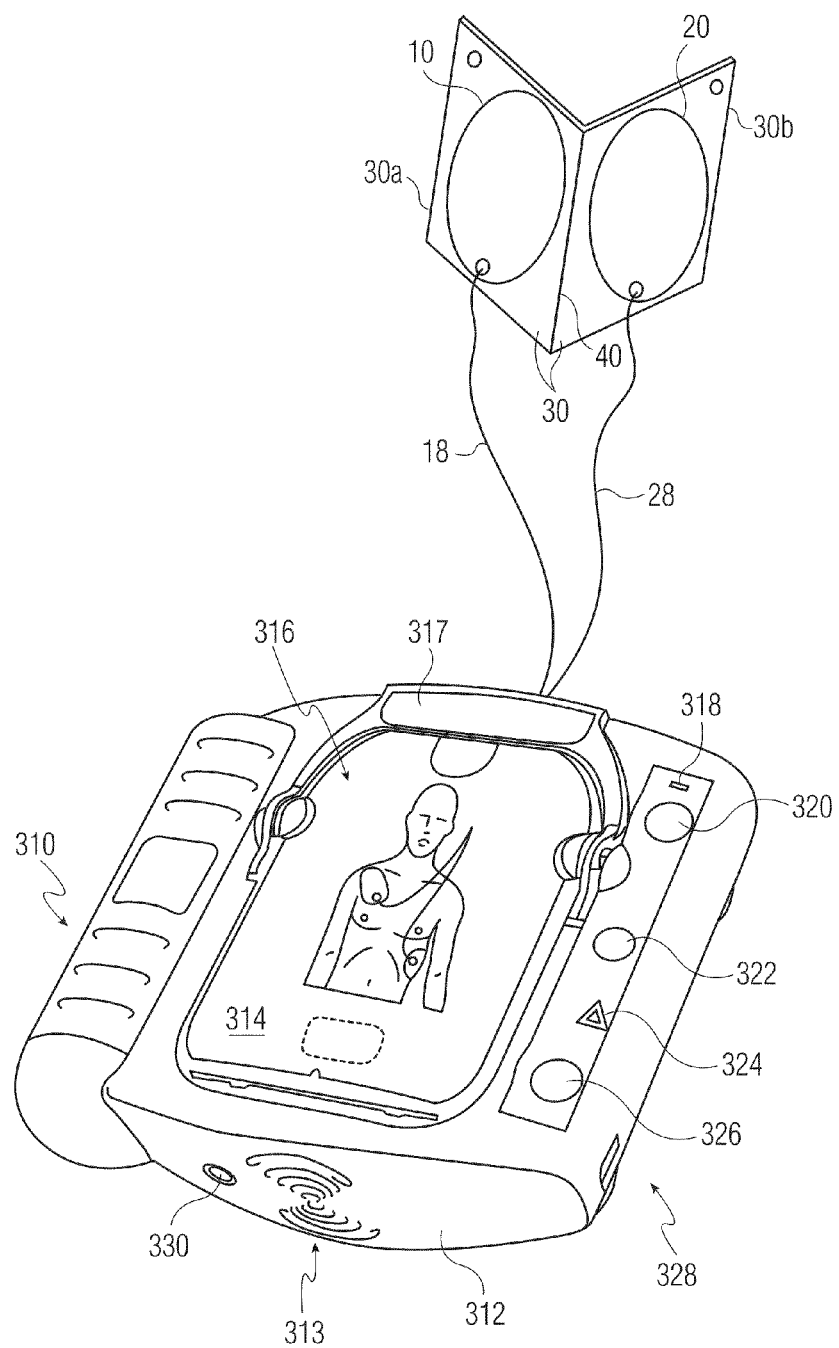
FIG. 4 illustrates a halibut-style release liner and electrodes connected to an AED.

FIG. 4 illustrates halibut electrodes of the present invention coupled to a defibrillator 310. The defibrillator 310 represents a semi-automatic external defibrillator (AED). However, other types of external defibrillators can be used as well. The AED 310 is housed in a rugged polymeric case 312 which protects the electronic circuitry inside the case, which was previously described with reference to FIG. 3, and also protects the rescuer from shocks. Attached to the case 312 by electrical leads 18,28 are a pair of halibut electrodes 10,20 attached to the two sides 30a,30b of a release liner 30. Prior to use the electrode pads 10,20 are retained in a cartridge 314 located in a recess on the top side of the AED 310. The electrode pads are accessed for use by pulling up on a handle 317 which allows removal of a plastic cover over the electrodes 10,20. The user interface is on the right side of the AED 310. A small ready light 318 informs the rescuer of the readiness of the AED 310. In this embodiment the ready light blinks after the AED 310 has been properly set up and is ready for use. The ready light is on constantly when the AED 310 is in use, and the ready light is off or flashes in an alerting color when the AED 310 needs attention.

Below the ready light is an on/off button 320. The on/off button is pressed to turn on the AED 310 for use. To turn off the AED 310 the rescuer holds the on/off button down for one second or more. An information button 322 flashes when information is available for the rescuer. The rescuer depresses the information button to access the available information. A caution light 324 blinks when the AED 310 is acquiring heartbeat information from the patient and lights continuously when a shock is advised, alerting the rescuer and others that no one should be touching the patient during these times. A shock button 326 is depressed to deliver a shock after the AED 310 informs the rescuer that a shock is advised. An infrared port 328 on the side of the AED 310 is used to transfer data between the AED 310 and a computer. This data port finds used after the patient has been rescued and a physician desires to have the AED 310 event data downloaded to his or her computer for detailed analysis. A speaker 313 provides voice instructions to the rescuer to guide the rescuer through the use of the AED 310 to treat the patient. A beeper 330 is provided which "chirps" when the AED 310 needs attention such as electrode pad replacement or a new battery.

Figure 5A:
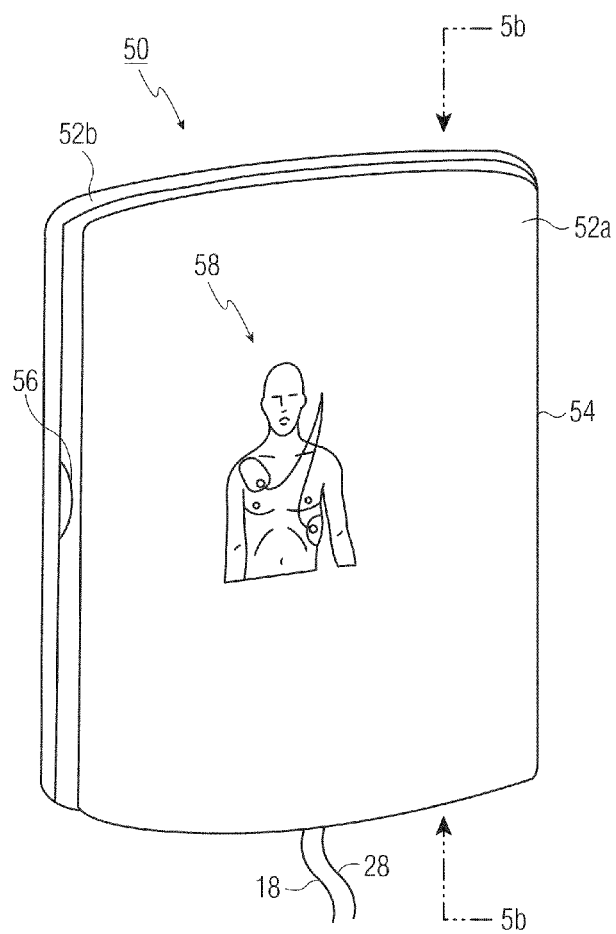
Figure 5B:
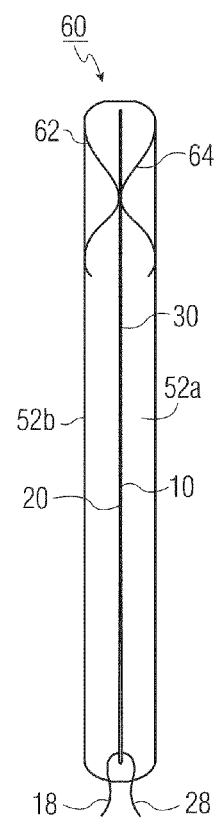

FIGS. 5a and 5b illustrate a case or cartridge 50 for storing halibut electrode pads prior to use in accordance with the principles of the present invention. The case 50 in this example is similar to the familiar cases which retain DVDs and can be made of a polymeric material, for instance. The two halves of the case 52a,52b are hinged together at one side by a hinge 54 and can be opened by depressing an indentation 56 on the other side of the case. While the case can be made to seal airtight as by the use of a gasket where the two halves come together or can be shrink-wrap sealed, this is not necessary as the peripheral sealing of the electrode pads 10,20 to a release liner 30 of polymeric or other moisture impermeable material will provide the necessary hermetic sealing of the electrode gel prior to use. A torso illustration 58 on the case illustrates the proper attachment of the electrodes to the patient.

The cross-sectional view of FIG. 5b shows that there is a spring clip 60 or other fastening device located inside the case. The two halves 62,64 of the spring clip are forced together when the case is closed, clamping the release liner 30 between them at the location of the holes 36,38. When the release liner is folded so that the two holes 36,38 oppose each other, this clamping action maintains contact of the two conductive sheets 44 of the release liner, completing the closed electrical circuit between the two electrode pads for self-test by a defibrillator attached to the electrical wires or leads 18,28. The case can also be used if the electrodes are not to be electrically connected by folding the release liner so that the holes are on the outside facing away from each other, in which case the clip 60 functions to retain the halibut electrodes and release liner in the case with no electrical connection between them. Thus, the same case 50 and halibut electrodes 10,20 and release liner 30 can be used for defibrillators which require and do not require electrical connection between the electrodes, simply by the way in which the release liner is folded inside the case.

Figure 6A:
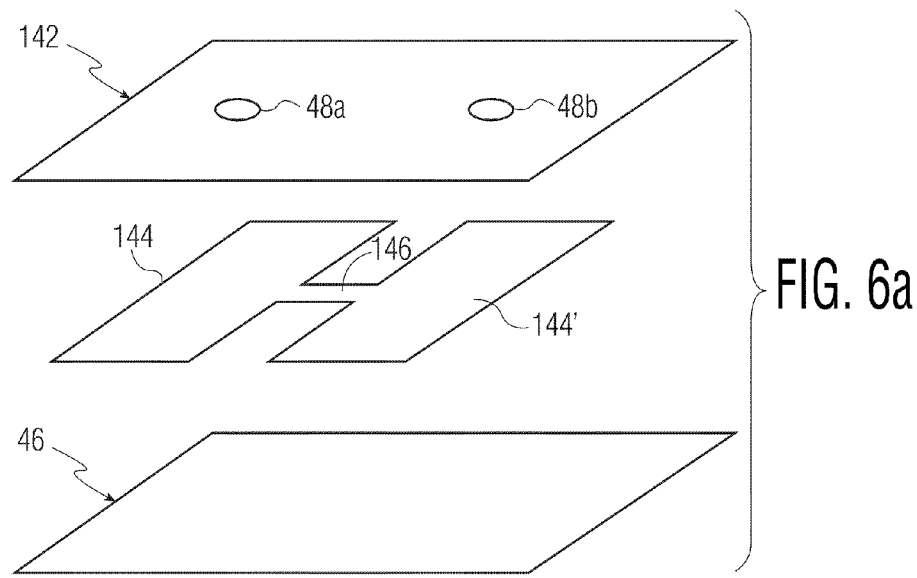
FIG. 6a illustrates a second example of a release liner of the present invention in an exploded view.
Figure 6B:
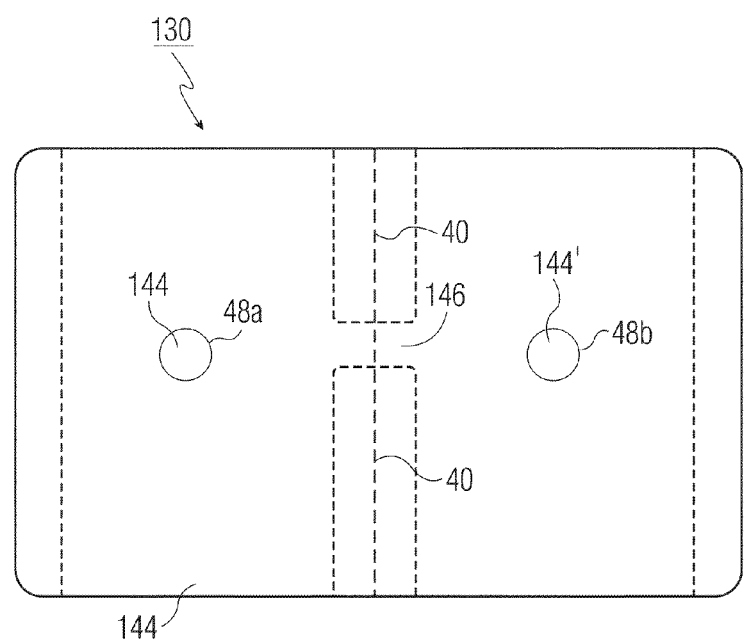
FIG. 6b is a plan view of the release liner of FIG. 6a after assembly and configured for a closed circuit connection to a defibrillator.

FIGS. 6a and 6b illustrate another example of a release liner for halibut electrodes of the present invention. In the exploded view of FIG. 6a the nonconductive release surface layer 142 of the release liner is seen to have only two holes, the holes 48a and 48b which underlie the electrodes when they are sealed to the layer 142 and permit electrical contact to an inner conductive sheet located between the outer nonconductive layers 142 and 46. The inner conductive sheet is composed of two sides 144 and 144' which underlie the holes 48a and 48b which are joined by a bridging portion 146. Thus the conductive sheet forms a continuous electrical connection between the two electrodes when they are attached to the release liner, as is evident from the plan view of the assembled release liner 130 of FIG. 6b. When the electrodes are attached to the surface 142 of the release liner 130 they are electrically connected to each other and ready for use with a defibrillator which requires electrically interconnected electrodes.

Figure 7A:
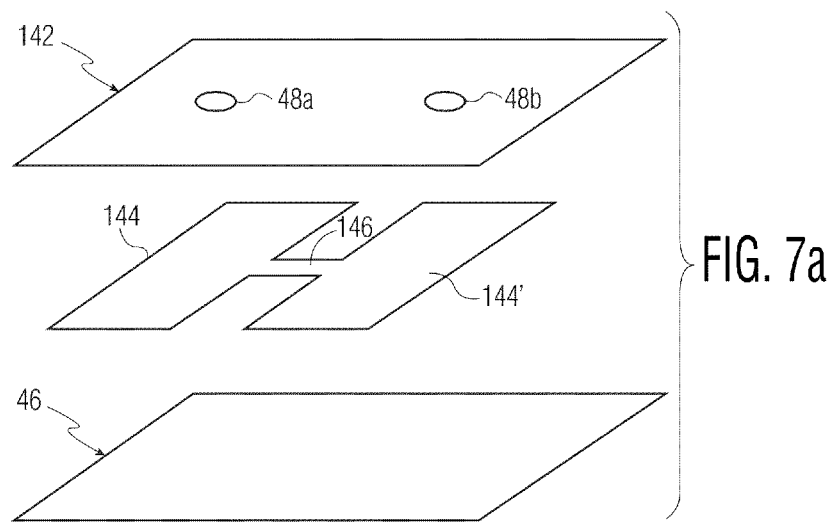
FIG. 7a illustrates the second example of a release liner of the present invention in an exploded view.
Figure 7B:
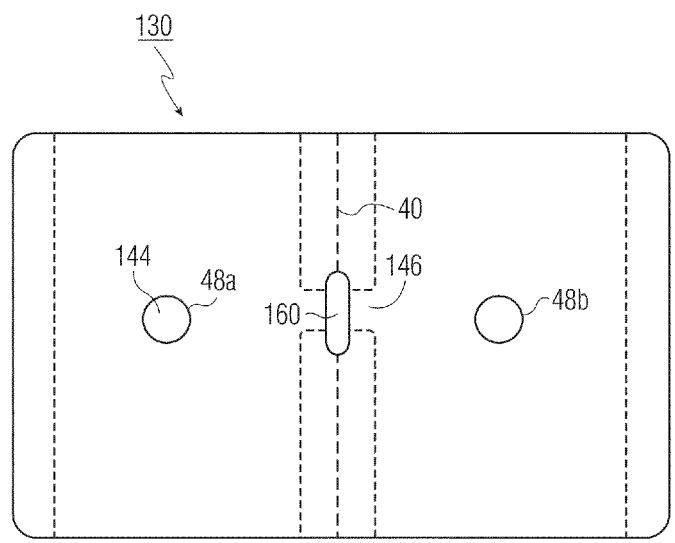
FIG. 7b is a plan view of the release liner of FIG. 7a after assembly and configured for an open circuit connection to a defibrillator.

The release liner configuration of FIGS. 6a and 6b can be converted to one in which the attached electrodes are not electrically interconnected as shown in FIGS. 7a and 7b. This is done by breaking the electrical connection between the two sides of the release liner 130. In the example of FIG. 7b this is done by punching a hole 160 through the release liner which severs the bridging portion 146 between the two halves 144 and 144' of the inner conductive sheet. The two halves 144 and 144' of the conductive sheet are thus no longer electrically connected to each other. Unlike the embodiment of FIGS. 1, 2a and 2b, the electrical interconnection or lack thereof is not determined by the manner in which the release liner is folded; it is determined by whether the two halves of the conductive sheet remain connected or are disconnected. The example of FIGS. 6a, 6b, 7a and 7b can be folded or unfolded in either configuration. Also unlike the earlier embodiment, the severing of the two halves of the conductive sheet make the non-interconnected configuration permanent, absent means to reconnect the two halves of the conductive sheet. Another way to view the two embodiments is that the two halves of the conductive sheet are nominally not connected in the FIGS. 1, 2a, 2b embodiment and nominally electrically connected in the FIGS. 6a, 6b, 7a, 7b embodiment. Breaking the electrical connection of the latter changes the configuration to use defibrillators requiring non-connected electrodes. For example, at the end of the manufacturing process the two halves of the conductive sheet can be left connected and the halibut electrodes used with defibrillators requiring electrically connected electrodes, or the bridging portion 146 can be cut and the halibut electrodes used with defibrillators requiring electrically disconnected electrodes. The same electrode manufacturing line can thus make electrodes for both types of defibrillators.

Figure 8A:
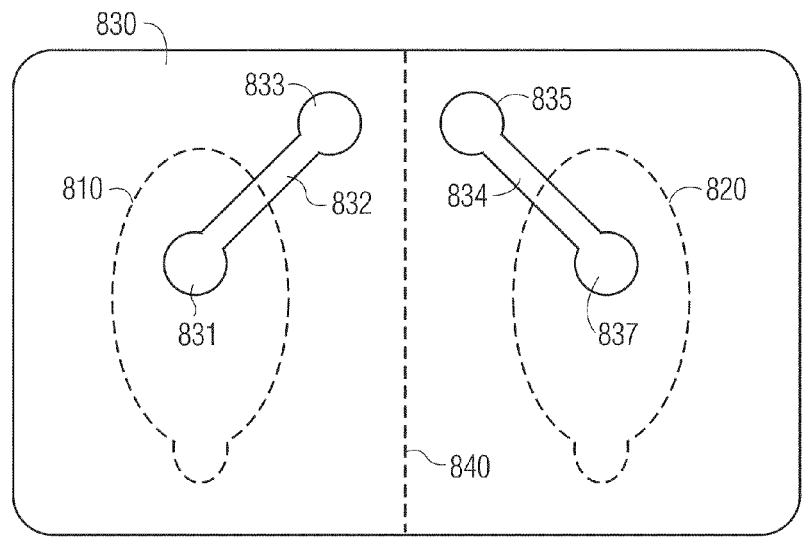
FIG. 8a is a plan view of a halibut release liner which is folded to electrically connect the electrodes and uses a single release liner sheet.

FIG. 8*a* is another example of a halibut release liner of the present invention. In this example the release liner comprises a single sheet 830 of moisture impermeable material to which electrodes are attached as above with the conductive gel facing the sheet. When the electrodes are peripherally sealed to the release liner sheet 830 the conductive gel of the electrodes is sealed as before between the moisture impermeable backing of the electrode and the moisture impermeable release liner sheet 830, protecting the gel from desiccation. Dashed lines 810 and 820 indicate the areas of the release liner where the electrodes are to be attached. The release liner sheet 830 may be formed of a polymeric or plastic material or other material that is nonconductive. Conductors 832 and 834 formed of thin foil, metallized ink, or other thin conductor is laminated or printed on the sheet with a portion of each positioned to contact the electrically conductive (gel) surface of the electrode and another portion extending outside of the attachment areas of the electrodes. In this example the conductors each have one rounded end 831,837 which makes contact with the conductive gel of an attached electrode and another rounded end 833,835 outside of the attachment areas 810,820. In this example the conductors 832,834 are laminated or printed on the side of the sheet 830 where the electrodes are to be attached, but they could also be located on the opposite side of the sheet 830 and make electrical contact through holes in the sheet. The conductors could also be embedded or molded into the sheet 830. The electrodes can be attached on the same side or on opposite sides of the sheet 830.

When the electrodes are attached in the electrode attachment areas 810 and 820, each attached electrode will be in electrical contact with a respective one of the conductors 832 and 834. When the sheet 840 is folded along fold line 840 so that conductor ends 833 and 835 are brought into contact with each other, the electrodes will be electrically connected to each other for a defibrillator which requires electrically connected electrodes for self-test. But when the sheet is folded the other way or left unfolded so that there is no electrical contact between conductors 832 and 834, the electrodes and release liner are suitable for connection to a defibrillator which does not require or cannot have preconnected electrodes electrically connected to each other.

The release liner sheet 830 can be opaque, translucent, or transparent. A transparent sheet will enable a user to visually inspect the conductive gel of the electrodes through the sheet 830 while the electrodes are attached to the release liner to discern any deterioration of the gel. The gel may contain a substance or material which changes color or otherwise changes visually when the moisture content of the gel changes, providing a quick and easy means for determining whether the electrodes are suitable for use.

Figure 8B:
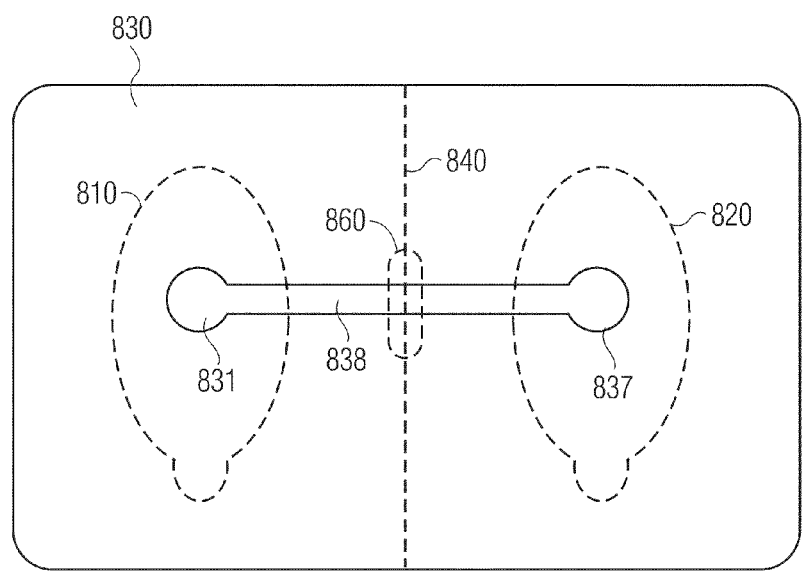
FIG. 8b is a plan view of a halibut release liner which is punched or cut to electrically disconnect the electrodes and uses a single release liner sheet.

FIG. 8*b* is another example of the present invention which, as in the example of FIG. 8*a*, uses a single release liner sheet 830. Instead of separate conductors, a conductor 838 is laminated to, printed on, or embedded in the sheet 830 and extends between the attachment position 810 for one electrode and the attachment position 820 for the other electrode. As before, the conductor 838 is preferably on the same side of the sheet 830 to which the electrodes are attached, but could also be on the other side and extend through the sheet to the two electrodes. When electrodes are attached to the release liner sheet 830 in the positions shown, the electrodes are electrically connected to each other by the conductor 838. If the conductor 838 is broken such as by punching a hole 860 through the conductor or through the conductor and the release liner sheet, the attached electrodes are rendered electrically disconnected with each other.

Other variations will readily occur to those skilled in the art. For instance, the conductors for the example of FIG. 8*a* could simply comprise small conductors at the locations and of the size of ends 831 and 837 with holes in sheet 830 behind the conductors providing access to conductors 831 and 837 on the back of sheet 830. When the release liner sheet 830 is folded back-to-back, the conductors 831 and 837 can be brought into contact with each other through the holes in the sheet 830 and clamped or attached into continuous contact to electrically connect the two electrodes. Folding the sheet the opposite way or leaving the sheet unfolded would leave the electrodes electrically disconnected with each other. Other variations of the examples described above are also possible.

The clip 150 of FIG. 2*b* can be used to retain the release liner of FIG. 8*a* in its desired folded configuration, either with the two electrodes electrically connected or folded with the two electrodes electrically separated. Likewise the case of FIGS. 5*a* and 5*b* can be used to protect and retain the release liner of FIG. 8*a* in either folded configuration. For the variation described in the previous paragraph which only has small conductors 831,837 located under the electrodes and accessible at the back of the release liner 830 through holes in the release liner sheet, the spring clip 60 or other retention device inside the case will be aligned with the conductors 831,837 so that the desired electrical contact through the holes of the release liner sheet is maintained by contact of the conductors 831 and 837.

Turning now to FIG. 9, an alternate embodiment of a defibrillator electrode assembly 400 constructed in accordance with the principles of the present invention is shown. Two electrodes 410 and 420, of similar construction to aforedescribed electrodes 10, each have a wire lead 418, 428, that electrically connects each electrode's inner conductive layer to a defibrillator such as that shown in FIG. 4. Each electrode 410, 420 has a conductive adhesive gel layer 412, 422 which is attached gel-side down on opposite sides 432, 434 of a non-conductive release liner 430. In a preferred embodiment, the electrodes are hermetically sealed, by heat seal or adhesive, to the release liner around their periphery, in order to prevent the gel layer from drying out during storage.

Release liner 430 has an opening 436 which is overlaid on each side by gel layers 412, 422. Release liner 430 is sufficiently thick, however, to prevent physical or electrical contact between gel layers 412, 422 across the thickness of the liner opening.

Non-conductive release liner 430 optionally includes an electrode guide key 438. As shown in later FIG. 13*a*, guide key 438 functions to ensure that the electrode assembly 400 is stored in the correct orientation.

Release liner 430 also may include a connector storage slot 495. The slot 495 mates to a corresponding tab formed in a defibrillator connector 484 (shown in FIG. 13*b*) to facilitate compact and neat storage of the defibrillator electrode assembly 400 during shipment.

As will be appreciated by one skilled in the art, a wide variety of substrates may be used to form non-conductive release liner 430. Typically, such non-conductive release liner material is chosen such that the electrically conductive gel layer 412, 422 of the electrode will readily peel away from the non-conductive release liner 430 while remaining attached to the electrode 410, 420. In some preferred embodiments, the non-conductive release liner 430 is about one millimeter in thickness, and constructed of a polymeric formed sheet of high-density poly-ethylene, a coated paperboard, or foam, such that the backing provides a relatively rigid surface with respect to the flexible electrode which is peeled away from the backing just prior to use.

To facilitate ease of removal of each electrode 410, 420 from each side 432, 434 of the release liner 430, the non-conductive release liner 430 comprises a material treated with an adhesion-reducing agent such as a surface-treated polymeric sheet. For example, the non-conductive release liner 430 may comprise siliconized polyethylene, polypropylene, polyester, acrylate, polycarbonate, or wax or plastic coated paperboard or foam. An adhesion-reducing agent as used herein refers to an agent that, when applied to a substrate, reduces the coefficient of friction of that substrate.

In embodiments using a heat-sealable material to seal the electrodes 410, 420 to the release liner 430, the release liner 430 may comprise an uncoated or non-surface treated substrate from which the heat-sealable material will readily peel off. In other embodiments, at least a portion of the release liner 430 that comes into contact with the electrically conductive gel layer of the electrode is coated with an adhesion-reducing material such that the gel separates cleanly from the liner surface. Other portions of the release liner 430 that are sealed directly to the heat-sealable layer are left uncoated since it is desired that a strong heat seal be maintained between the release liner 430 and the heat-sealable layer during extended storage.

FIGS. 10 and 11 illustrate two embodiments of a storage case 450, 550 for defibrillator electrode assembly 400, 500. FIG. 10 illustrates a generally rectangular storage case 450 having an opening 452 along the long edge of the case that is arranged to receive defibrillator electrode assembly 400 for storage prior to use. Storage case 450 is also arranged to hold an optional pinch clip 460. When pinch clip 460 is installed over portals in one or both faces of storage case 450, the dome ends of clip 460 extend partially into and constrict the case 450 interior. Clip 460 is preferably of a spring-type material, such as stainless steel. The dome ends of clip 460 are preferably smooth and hemispherical in order to allow the electrode assembly 400 to be slidably inserted between the respective pinch clip ends. In this stored configuration, compression force is exerted by the pinch clip dome ends against each electrode 410, 420.

An alternate embodiment of a rectangular storage case 550 is shown in FIG. 11. Storage case 550 and an optional pinch clip 560 function similarly to storage case 450 and pinch clip 460, except that storage case 550 is arranged to receive defibrillator electrode assembly 400 through an opening 552 at the short edge of the case for storage prior to use.

Storage cases 450, 550 are preferably constructed of a polycarbonate plastic or like material which is rigid enough to protect the electrode assembly 400 from damage or puncture. A drain hole may be formed in the bottom of the case to allow egress of water and debris. In addition, each storage case may comprise an optional electrode guide slot 458 which mates with electrode guide key 438 on non-conductive release liner 430 to ensure that the electrode assembly 400 is inserted into the case in the correct orientation. The storage cases may also include a molded-in "snap" feature which gives the installer tactile feedback that the electrode assembly 400 is fully and properly inserted.

FIGS. 12a through 12d illustrate representative cross-section views showing the functional interaction between electrode assembly 400 and storage case 450. FIG. 12a is a cross sectional view of the electrode assembly 400, showing the non-conductive release liner 430 having a thickness t to which electrodes 410, 420 are sealed on liner 430 first side 432 and second side 434 respectively. In this un-stored configuration, electrode gel layers 412 and 422 are exposed to each other through opening 436, but remain separated across the gap 440 of thickness t. Thus it is seen that any continuous closed loop circuit between electrodes is prevented by gap 440.

FIG. 12b is a cross section view of storage case 450 with pinch clip 460 installed. Pinch clip 460 may be disposed on each side of storage case 450, or as indicated by the dashed line, may be a single action pinch clip 462 that is installed on just one side. The distance between parallel interior walls 454, 456 is slightly wider than electrode assembly 400 which is slidably installed therein, as shown in FIG. 12c. It can be seen that when installed properly, pinch clip 460 compresses electrode gel layers 412, 422 into electrical contact with each other through opening 436. This forms an electrical circuit through defibrillator connector 484 with defibrillator 310 which can be used for self-test during storage and for pads state sensing during use.

FIG. 12d is a cross sectional view of the same storage case 450 without pinch clip 460 installed. There it is seen that electrode assembly 400 may be stored in the same case 450, but without the gel layers 412, 422 being compressed together. This configuration allows the pre-connected storage of electrodes to defibrillators which are not configured to self-test electrodes.

Figure 13A:
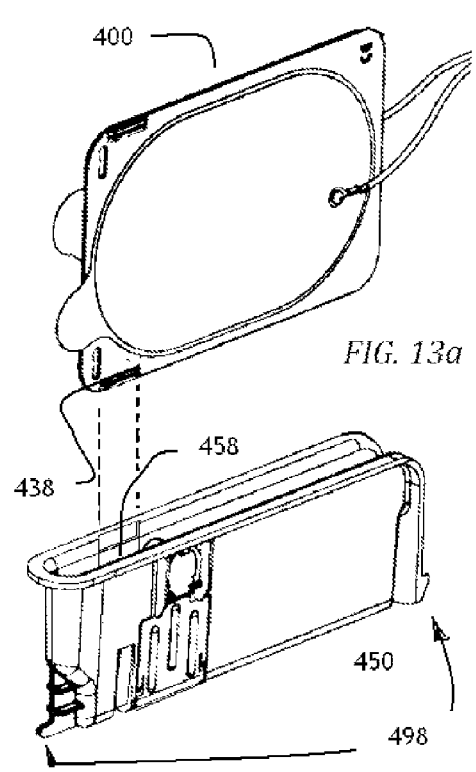
FIG. 13 is a perspective view of an electrode assembly and storage case with various features for improved storage prior to use.
Figure 13B:
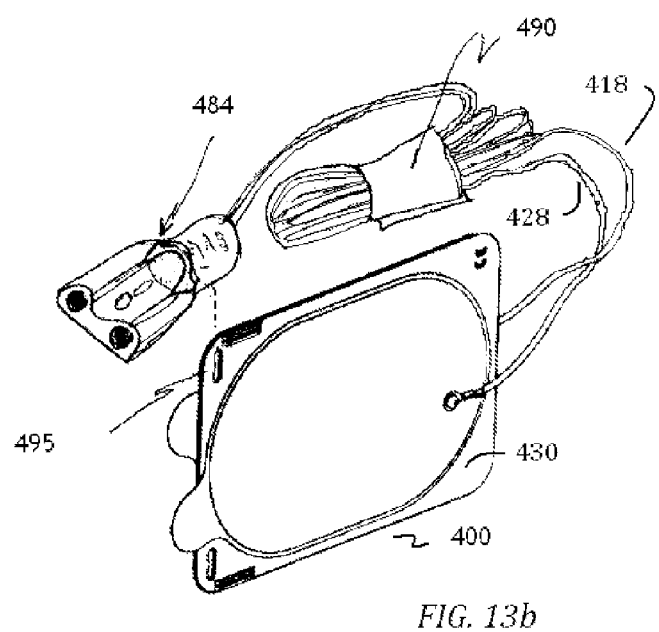
Figure 14:
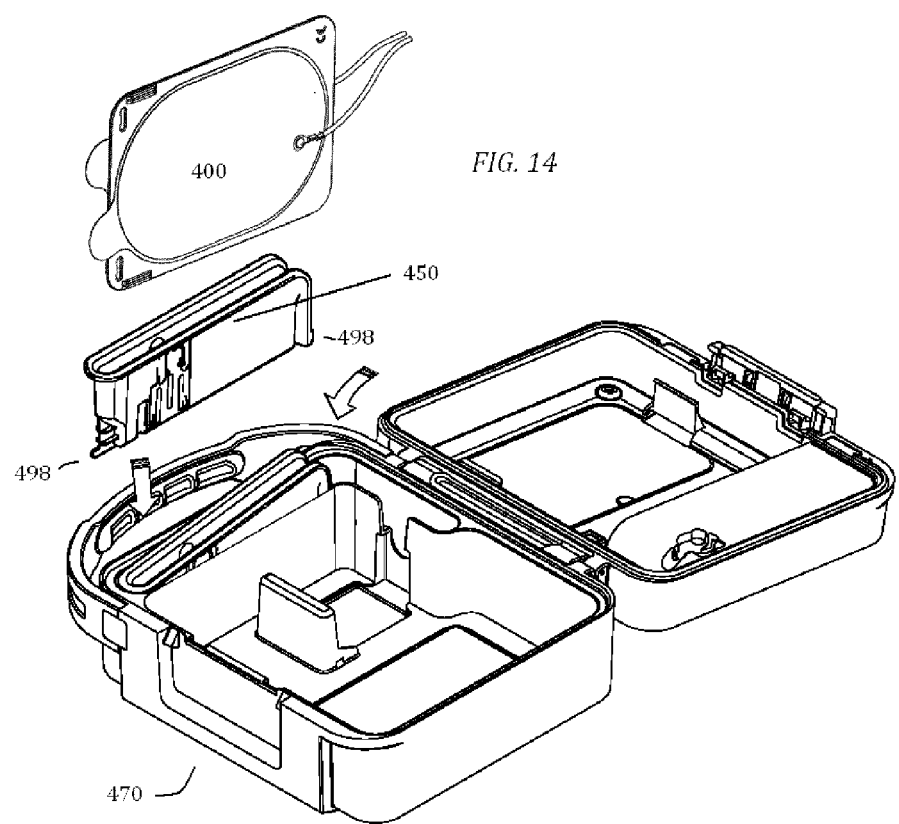
FIG. 14 is a perspective view of an electrode assembly disposed in a defibrillator carrying case.

FIGS. 13a and 13b illustrate additional embodiments of electrode assembly 400 and storage case 450. As shown in FIG. 13a, the electrode guide key 438 in electrode assembly 400 mates with corresponding electrode guide slot 458 in case 450 to ensure the correct storage orientation. In addition, storage case 450 is shown with exterior connection clips 498 for secure attachment of the entire electrode and case assembly inside an associated defibrillator storage case 470. FIG. 14 illustrates an exemplary embodiment of such an arrangement.

FIG. 13b illustrates additional embodiments of electrode assembly 400. An electrode lead wrap 490 is shown, which functions to hold the electrode leads 418, 428 in a neat bundle during storage. Lead wrap 490 is preferably constructed of paper or plastic wrap, which tears away and frees the electrode lead wires 418, 428 when a user deploys the electrode assembly 400 during a rescue.

Also shown in FIG. 13b is a defibrillator connector storage slot 495 formed in release liner 430, into which a tab on defibrillator connector 484 is fitted. Thus the connector 484 is held securely to release liner 430 during shipment.

Each of the lead wrap 490 and storage slot 495 function to minimize clutter, which could otherwise introduce delay during a rescue use. The lead wrap 490 and slot 495 also help to prevent inadvertent pulling of the electrode wires which might damage or prematurely unseal the electrodes 410, 420 from release liner 430.

It may be desirable to store the electrode assembly 400 in a fixed relation to an attached defibrillator, in order to protect the electrode and lead wires from damage. FIG. 14 illustrates one such exemplary embodiment in the form of a defibrillator carrying case 470. Defibrillator carrying case 470 comprises a storage compartment that holds storage case 450. Exterior connecting clips 498 mate with corresponding attachments on the carrying case to hold storage case 450 securely in place. Electrode assembly 400 is inserted into storage case 450 and connected to a defibrillator co-located inside (not shown). The closed carrying case 470 thereafter protects defibrillator, electrode and leads prior to use.

Other variations to the inventions shown and described will readily occur to those skilled in the art. For example, the pinch clip may be formed as part of the storage case. The relative placement of guide slots and guide keys, as another example, may be readily adjusted to account for dimensional requirements of the electrode and storage environments.

What is claimed is:

1. A defibrillator system having an ECG circuit which receives ECG signal and a shock delivery circuit which delivers a shock to electrodes, and having an electrode assembly comprising:
   a non-conductive release liner having a first side, a second side, a thickness, and an opening through the thickness from the first side to the second side;
   a first electrode having a first conductive gel layer disposed in contact with the release liner first side and overlaying the opening;
   a second electrode having a second conductive gel layer disposed in contact with the release liner second side and overlaying the opening, such that the first and second gel layers oppose each other through the opening in the thickness;
   first and second electrode leads extending from respective first and second electrodes for electrically connecting the electrodes to a defibrillator circuit;
   a storage case into which the release liner, first electrode and second electrode are inserted; and
   a clip disposed on the interior of the storage case at the location of the release liner opening which retains the first and second gel layers in contact with each other through the opening,
   wherein an end of the clip extends partially into the interior of the storage case in about the amount of the thickness of the non-conductive release liner.

2. The defibrillator system electrode assembly of claim 1, wherein the clip comprises a pinch clip operable to press the first gel layer and second gel layer into electrical contact through the opening when the release liner, first electrode and second electrode are retained in the storage case.

3. The defibrillator system electrode assembly of claim 2 wherein the pinch clip is removable.

4. The defibrillator system electrode assembly of claim 2 wherein the pinch clip constricts an interior dimension of the storage case at the location of the release liner opening.

5. The defibrillator system electrode assembly of claim 2 wherein the pinch clip presses the electrode assembly from both sides of the opening when the release liner, first electrode and second electrode are inserted into the storage case.

6. The defibrillator system electrode assembly of claim 2 wherein the pinch clip presses the electrode assembly from one side of the opening when the release liner, first electrode and second electrode are inserted into the storage case.

7. The defibrillator system electrode assembly of claim 1 further comprising:
   an electrode lead wrap for removably securing the first and second electrode leads in a bundle; and
   a defibrillator connector electrically connected to the first and second electrode leads for connecting the electrode assembly to a defibrillator circuit.

8. A The defibrillator system of claim 1, further comprising:
   a self-test circuit, coupled to the first and second electrodes, which operates on an electrical circuit completed by the contact of the first and second gel layers through the opening;
   and further comprising:
   a defibrillator connector electrically connecting the selftest circuit to the first electrode lead and the second electrode lead.

9. The defibrillator system of claim 8, wherein the selftest circuit is an electrode self-test circuit, and further wherein the clip comprises
   a pinch clip which presses the first gel layer and second gel layer into electrical contact through the release liner opening, thereby completing the electrode self-test circuit.

10. A defibrillator system having an ECG circuit which receives ECG signal and a shock delivery circuit which delivers a shock to electrodes, and having an electrode assembly comprising:
    a non-conductive release liner having a first side, a second side, a thickness, and an opening through the thickness from the first side to the second side;
    a first electrode having a first conductive gel layer disposed in contact with the release liner first side and overlaying the opening;
    a second electrode having a second conductive gel layer disposed in contact with the release liner second side and overlaying the opening, such that the first and second gel layers oppose each other through the opening in the thickness;
    first and second electrode leads extending from respective first and second electrodes for electrically connecting the electrodes to a defibrillator circuit; and
    a storage case into which the release liner, first electrode and second electrode are inserted; the storage case further comprising a clip disposed on the interior of the storage case at the location of the release liner opening which retains the first and second gel layers in contact with each other through the opening,
    wherein the clip comprises a pinch clip operable to press the first gel layer and second gel layer into electrical contact through the opening when the release liner, first electrode and second electrode are retained in the storage case,
    wherein the pinch clip constricts an interior dimension of the storage case at the location of the release liner opening, and
    wherein the pinch clip constricts the interior dimension of the storage case in the amount of the thickness of the release liner.

* * * * *